United States Statutory Invention Registration [19]

[11] Reg. Number: H266

Starchild [43] Published: May 5, 1987

[54] METHOD OF CEREBROSPINAL FLUID TRANSFUSION

[76] Inventor: Adam A. Starchild, Box 5474, New York, N.Y. 10163

[21] Appl. No.: 912,099

[22] Filed: Sep. 29, 1986

[51] Int. Cl.[4] ..... A61M 5/00

[52] U.S. Cl. ..... 604/8

*Primary Examiner*—Deborah L. Kyle
*Assistant Examiner*—Michael J. Carone

[57] ABSTRACT

A method of transfusing human cerebrospinal fluid, wherein the blood types of the donor and donee may be used to match compatible cerebrospinal fluid.

1 Claim, No Drawings

---

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

METHOD OF CEREBROSPINAL FLUID TRANSFUSION

SUMMARY OF THE INVENTION

The principal discovery is that human brain fluid and blood groups fully coincide, providing a method for the transfusion of cerebrospinal fluid.

DETAILED DESCRIPTION

Classical literature contends that cerebrospinal fluid contains no specific anti-genes and anti-bodies and cannot therefore be grouped. In early experiments with transfusion of cerebrospinal fluid it was administered into the skin or into a vein.

An important feature of this invention is that drops of cerebrospinal fluid mixed with reference erythrocytes representing different blood groups agglutinate, demonstrating that it divides into groups the same as blood.

There is therefore no need to make a lumbar puncture to establish the cerebrospinal group because the test of blood from a finger will do.

The discovery of groups for cerebrospinal fluid determines that transfusions are to be administered neither into the vein nor under the skin, as was done previously, but directly into those cavities where it is found. Approximately 20 grams are needed.

The transfusion of cerebrospinal fluid can help treat people with diseases that are otherwise difficult to treat; can influence their emotional state, memory and metabolism; and strengthen the body's immune systems.

What is claimed is:

1. A method of transfusing cerebrospinal fluid comprising the steps of: Matching the blood types of a donor and donee and transfusing cerebrospinal fluid from the donor to the donee.

* * * * *